United States Patent
Luo et al.

(10) Patent No.: US 7,538,322 B2
(45) Date of Patent: May 26, 2009

(54) METHOD OF FABRICATING SAMPLE MEMBRANES FOR TRANSMISSION ELECTRON MICROSCOPY ANALYSIS

(75) Inventors: Jian-Shing Luo, Penghu County (TW); Lang-Yu Huang, Hsinchu County (TW)

(73) Assignee: Inotera Memories, Inc., Taoyuan (TW)

( * ) Notice: Subject to any disclaimer, the term of this patent is extended or adjusted under 35 U.S.C. 154(b) by 250 days.

(21) Appl. No.: 11/556,198

(22) Filed: Nov. 3, 2006

(65) Prior Publication Data

US 2008/0054179 A1    Mar. 6, 2008

(30) Foreign Application Priority Data

Sep. 6, 2006    (TW) ............... 95132838 A

(51) Int. Cl.
*G01N 1/28* (2006.01)
*G01N 23/04* (2006.01)

(52) U.S. Cl. ................ 250/304; 250/307; 250/311; 73/866.5

(58) Field of Classification Search ................ 250/306, 250/307, 309–311, 423 F, 440.11, 492.1, 250/492.2, 492.21, 492.3; 73/863, 866.5
See application file for complete search history.

(56) References Cited

U.S. PATENT DOCUMENTS

| | | | | |
|---|---|---|---|---|
| 4,777,364 A | * | 10/1988 | Sartore | 250/307 |
| 5,767,516 A | * | 6/1998 | Kawanami et al. | 250/311 |
| 5,892,225 A | * | 4/1999 | Okihara | 250/311 |
| 5,986,264 A | * | 11/1999 | Grunewald | 250/310 |
| 6,335,533 B1 | * | 1/2002 | Morales et al. | 250/492.2 |
| 6,570,170 B2 | * | 5/2003 | Moore | 250/492.21 |
| 7,172,807 B2 | * | 2/2007 | Fukano et al. | 428/216 |
| 7,395,727 B2 | * | 7/2008 | Moore | 73/866.5 |
| 2002/0048696 A1 | * | 4/2002 | Kukino et al. | 428/698 |
| 2002/0121614 A1 | * | 9/2002 | Moore | 250/492.1 |
| 2006/0270067 A1 | * | 11/2006 | Lin | 438/5 |
| 2007/0194225 A1 | * | 8/2007 | Zorn | 250/306 |
| 2008/0054179 A1 | * | 3/2008 | Luo et al. | 250/304 |

\* cited by examiner

*Primary Examiner*—Bernard E Souw
(74) *Attorney, Agent, or Firm*—Jianq Chyun IP Office

(57) ABSTRACT

A method of fabricating sample lamella for transmission electron microscopy (TEM) analysis is provided. A waiting-examination sample having an analysis target on the top surface of that is offered, and at least a mark around the analysis target is defined. A covering layer is covered on the top surface of waiting-examination sample. A holder is attached on the covering layer. A backside polishing process is performed to remove a portion of the waiting-examination sample until the mark is visible under the optical microscopy from the bottom surface of waiting-examination sample. An in-situ lift-out step is performed to pick up a thin membrane containing the analysis target and serve as the sample for TEM analysis.

13 Claims, 3 Drawing Sheets

METHOD OF FABRICATING SAMPLE MEMBRANES FOR TRANSMISSION ELECTRON MICROSCOPY ANALYSIS

CROSS-REFERENCE TO RELATED APPLICATION

This application claims the priority benefit of Taiwan application serial no. 95132838, filed Sep. 6, 2006. All disclosure of the Taiwan application is incorporated herein by reference.

BACKGROUND OF THE INVENTION

1. Field of the Invention

The present invention relates to a semiconductor measurement and analysis technology. More particularly, the present invention relates to a method of fabricating sample lamella for transmission electron microscopy (TEM) analysis.

2. Description of Related Art

During the failure analysis and the process evaluation of VLSI (very large scale integration) device, cross-section analysis is considered as an effective technology. The scanning electron microscopy (SEM) is a tool for observing the cross-section, but the resolution is relatively weak for the high-density device. Therefore, when the semiconductor process progresses into the stage of VLSI, SEM are gradually replaced by TEMs. The TEMs are widely used in the failure analysis and process evaluation, so as to solve the problem concerning output and device reliability.

Generally speaking, in the TEM analysis technology, the fabrication of the sample lamella is one of the crucial steps. When a TEM is used for observing, the thickness of the sample membrane must be smaller than 0.1 μm, so as to provide the transmittance required by the electron transmission of TEM and to acquire clear images. Recently, the fabrication of the sample membrane for TEM analysis at a specific position must use a focused ion beam (FIB) thinning technology to perform a sample membrane thinning process, and in order to prevent the surface of a chip from being damaged by an ion beam, usually a Pt film (or a W film) is formed on the surface of the chip to block sputtering by the ion beam.

In another aspect, although the Pt film (or W film) can prevent the surface of the chip from being damaged by the ion beam, usually the Pt film (W film) is also formed by using an FIB depositing technology. In this method, when the Pt film (or W film) is formed, a damage layer is formed on the chip resulting in the damage of the defect structure to the chip, and thus the analysis of the defect is affected. Although an E-beam can be used to replace the FIB to perform the Pt film (or W film) deposition process, the method may also damage the top layer. Another prior art proposes forming a buffer layer on the chip, and then forming the Pt film (W film) on the buffer layer. However, it is difficult to locate when searching for the defects on the chip.

Therefore, it has become a problem to be solved in the industry as to how to easily fabricate the sample lamella for TEM analysis without damaging the defects on the chip.

SUMMARY OF THE INVENTION

Accordingly, the present invention is directed to provide a method of fabricating sample lamella for TEM analysis, which is capable of easily fabricating the sample lamella without damaging a defect structure and resulting in the problems of the defects and the difficulty in location.

The present invention provides a method of fabricating sample lamella for TEM analysis. In this method, a waiting-examination sample having an analysis target on the top surface is provided. Then, a covering layer is formed on the top surface of the waiting-examination sample. Afterward, a holder is formed on the covering layer. Thereafter, a backside polishing process is performed to remove a portion of the waiting-examination sample until the mark is visible under an optical microscope from the bottom surface of waiting-examination sample. An in-situ lift-out step is performed to fabricate a thin membrane containing the analysis target and the mark as the sample membrane for TEM analysis.

According to an embodiment of the present invention, the covering layer is, for example, an epoxy layer, an oxide layer, a nitride layer, a silicon material layer, or a metal layer. The method of forming the covering layer on the top surface of the waiting-examination sample comprises, for example, performing a chemical vapor deposition (CVD) process or a coating process.

According to an embodiment of the present invention, the holder comprises a glass holder. The process of forming the holder on the covering layer comprises, for example, using an adhesive. The adhesive is, for example, epoxy.

According to an embodiment of the present invention, the method of forming the mark comprises, for example, using a dual beam FIB or laser.

According to an embodiment of the present invention, the mark is, for example, a groove.

According to an embodiment of the present invention, the backside polishing process is, for example, a mechanical polishing process.

According to an embodiment of the present invention, the in-situ lift-out step is performed in the dual beam FIB system. In an embodiment, before the in-situ lift-out step is performed, the method further comprises forming a passivation layer on the waiting-examination defect region on the bottom surface of the waiting-examination sample. The material of the passivation layer comprises Pt or W.

According to an embodiment of the present invention, after the in-situ lift-out step is performed, the method further comprises performing a sample membrane thinning step.

According to the present invention, the backside polishing process and the in-situ lift-out step are used to fabricate the sample membrane, so that the analysis target is not damaged, and the analysis structure of the target on the fabricated sample membrane is intact. Thus, the reliability of the TEM analysis may be effectively promoted. Moreover, the fabrication method of the present invention is simple and is capable of fabricating the sample membrane for TEM analysis without damaging the target structure.

In order to make the aforementioned and other objects, features and advantages of the present invention comprehensible, preferred embodiments accompanied with figures are described in detail below.

DESCRIPTION OF EMBODIMENTS

The accompanying drawings are included to provide a further understanding of the invention, and are incorporated in and constitute a part of this specification. The drawings illustrate embodiments of the invention and, together with the description, serve to explain the principles of the invention.

Figure 1:
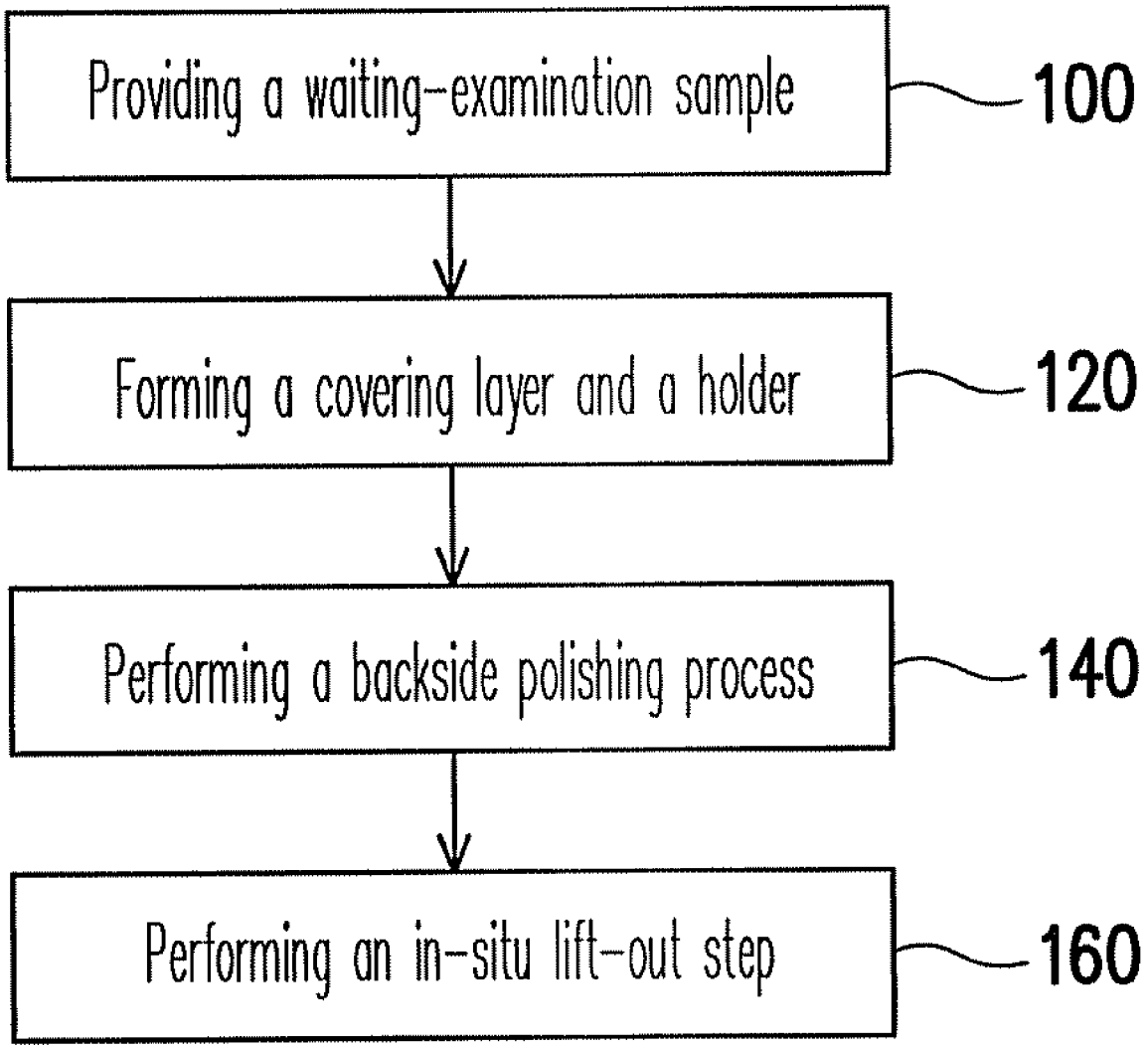
FIG. 1 is a flow chart showing the steps of the method of fabricating sample lamella for TEM analysis according to an embodiment of the present invention.

FIG. 1 is a flow chart showing the steps of the method of fabricating sample membrane for TEM analysis according to an embodiment of the present invention. FIGS. 2A to 2D are schematic sectional views of the process steps of the method of fabricating sample membrane for TEM analysis according to an embodiment of the present invention.

Figure 2A:
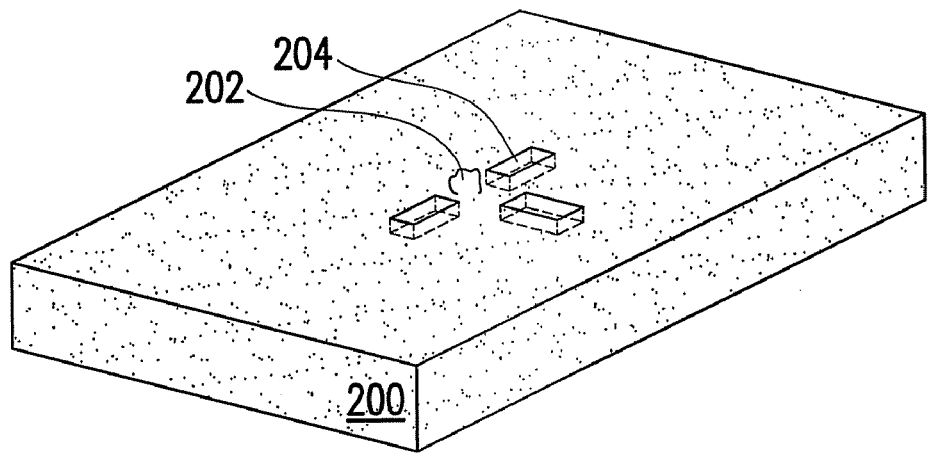
FIGS. 2A to 2D are schematic sectional views process steps of the method of fabricating sample membrane for TEM analysis according to an embodiment of the present invention.

First, referring to FIGS. 1 and 2A together, the method of fabricating the sample lamella for TEM analysis comprises the following steps. First, a waiting-examination sample 200 is provided (step 100). The waiting-examination sample 200 comprises, for example, a small portion of a wafer. Generally speaking, devices such as memories and metal oxide semiconductor transistors have been formed on the waiting-examination sample 200. Moreover, in the defect examination, usually a defect 202 is detected on the waiting-examination sample 200, so it is necessary to fabricate a specific region into the sample membrane for further analysis. The defect 202 on the waiting-examination sample 200 serves as the analysis target in the subsequent TEM analysis.

Moreover, a mark 204 is defined around the defect 202 formed on the waiting-examination sample 200. In this embodiment, for example, three "groove" marks 204 are defined on the waiting-examination sample 200. However, the quantity and shape of the mark are not limited as such. More particularly, the method of fabricating the waiting-examination sample 200 comprises, for example, using a positioning navigation system for a dual beam FIB or laser table to position the region predefined to form the sample membrane on the wafer. Next, a low current dual beam FIB or laser etc. is used to form the groove with a length of about 1 μm and a depth of about 3 μm around the defect 202 as the mark 204. Next, a 0.5×0.5 cm$^2$ region containing the defect 202 and the mark 204 is removed from the wafer by cutting or cleaving, which serves as the waiting-examination sample 200.

It should be noted that the mark is fabricated and positioned before forming the film layer on the defect 202 so that the problem of searching the position of the mark may be effectively avoided.

Figure 2B:
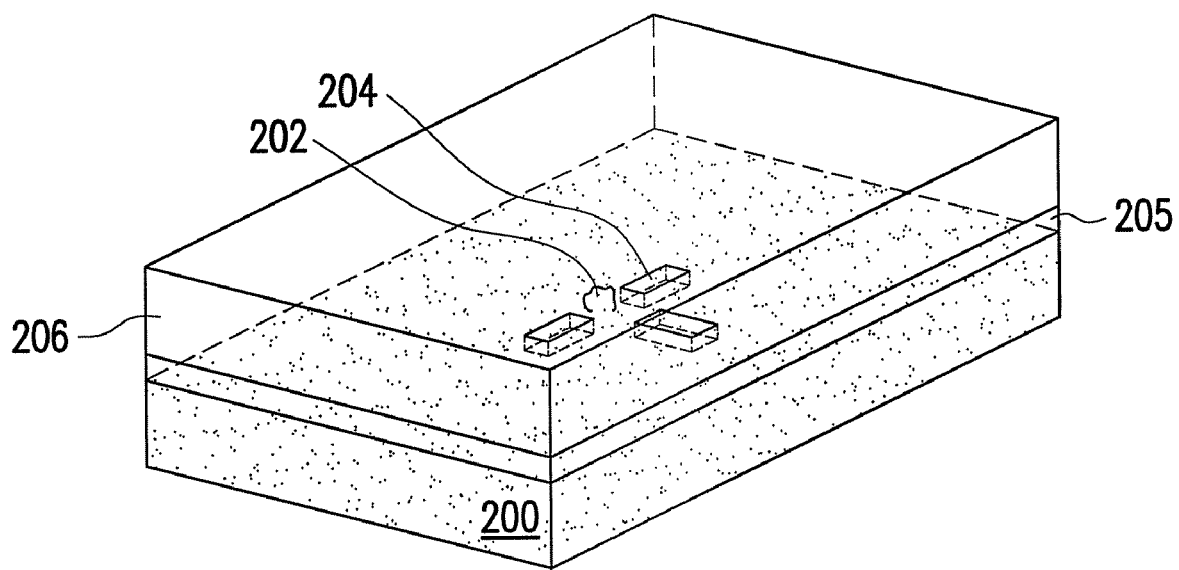

Next, referring to FIGS. 1 and 2B, after the waiting-examination sample 200 is fabricated, a covering layer 205 and a holder 206 are successively formed on the waiting-examination sample 200 (step 120). The covering layer 205 may serve to protect the defect 202 from being damaged in the subsequent process. The covering layer 205 comprises, for example, a material layer such as an epoxy layer, an oxide layer, a nitride layer, a silicon material layer, a metal layer, or another suitable material layer that may not damage the defect 202, and may be formed by, for example, performing a CVD process, coating process, or other suitable process. Moreover, the holder 206 can carry the whole waiting-examination sample 200 and the covering layer 205. The holder 206 may be comprised of, for example, a glass holder, and is adhered to the covering layer 205 by using an adhesive, for example, epoxy.

Figure 2C:
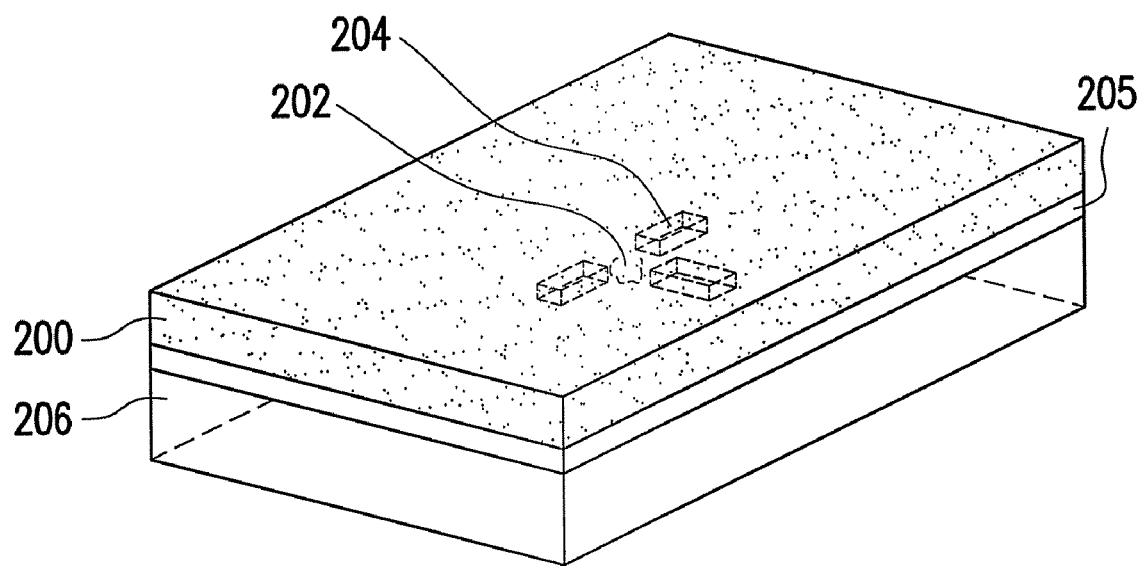

Thereafter, referring to FIGS. 1 and 2C together, after the covering layer 205 and the holder 206 are formed, a backside polishing process is performed on the waiting-examination sample 200 (step 140). In this embodiment, before performing the backside polishing process, a thermal wax can be used to attach the whole holder 206, the covering layer 205, and the waiting-examination sample 200 to a polishing base. The backside polishing process performed on the waiting-examination sample 200 includes, for example, a mechanical polishing process to polish one side of the waiting-examination sample 200 without the defect 202 to remove a top portion of the waiting-examination sample 200. During the backside polishing process, an optical microscopy technique may be used to monitor the thickness of the waiting-examination sample 200 and observe the mark 204. The backside polishing process and the monitoring step are continued until the mark 204 is visible from the backside of the waiting-examination sample 200 under the optical microscope.

Figure 2D:
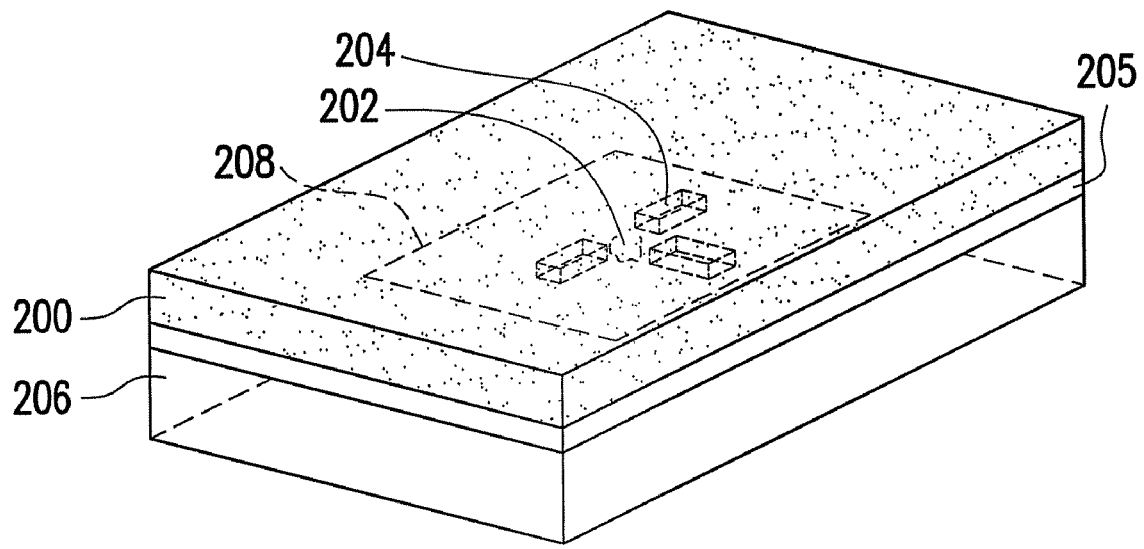

Next, referring to FIGS. 1 and 2D together, after performing the backside polishing process, an in-situ lift-out step is performed (step 160). In this embodiment, prior to performing the in-situ lift-out step, the above structure may be treated with acetone or other suitable solvents to separate the holder 206, the covering layer 205, and the waiting-examination sample 200 from the polishing base. Next, the in-situ lift-out step is performed, and the dual beam FIB is used to mill the backside of the waiting-examination sample 200 to obtain a thin membrane 208 containing the defect 202 and the mark 204 as the sample membrane for TEM analysis. Moreover, the thin membrane 208 may also include portions of the waiting-examination sample 200 and the cover layer 206. Accordingly, before performing the in-situ lift-out step, a passivation layer (not shown) may be formed on the backside of the waiting-examination sample 200. The material of the passivation layer is, for example, Pt, W or any other suitable material.

Particularly, the method of forming the sample lamella for TEM analysis is performed by milling the backside of the waiting-examination sample 200, so that the defect 202 on the waiting-examination sample 200 will remain undamaged.

In an embodiment, after the thin membrane 208 is formed, a thinning step is performed such that the thickness of the sample membrane for TEM analysis is suitable for TEM analysis.

It is known from the above description that the method of fabricating the sample lamella for TEM analysis of the present invention is capable of retaining the structure of the defect on the sample membrane intact and undamaged. Thus, the reliability of the TEM analysis may be effectively promoted. Further, the present invention uses simple process such as the backside polishing process and the in-situ lift-out step to fabricate the sample lamella for TEM analysis without damaging the structure of the defect. Thus, the overall fabrication cost may be effectively reduced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of fabricating sample lamella for transmission electron microscopy (TEM) analysis, comprising:
    providing a waiting-examination sample having an analysis target on a top surface thereof and at least a mark disposed around the analysis target;
    forming a covering layer on the top surface of the waiting-examination sample;
    forming a holder on the covering layer;
    performing a backside polishing process to remove a portion of the waiting-examination sample until the mark is visible from the bottom surface of the waiting-examination sample under an optical microscope; and performing an in-situ lift-out step to obtain a thin membrane containing the analysis target and the mark to serve as a sample membrane for TEM analysis.

2. The method of fabricating sample lamella for TEM analysis as claimed in claim 1, wherein the covering layer comprises an epoxy layer, an oxide layer, a nitride layer, a silicon material layer, or a metal layer.

3. The method of fabricating sample lamella for TEM analysis as claimed in claim 2, wherein the method of forming the covering layer on the top surface of the waiting-examination sample comprises performing a chemical vapor deposition (CVD) process or a coating process.

4. The method of fabricating sample lamella for TEM analysis as claimed in claim 1, wherein the holder comprises a glass holder.

5. The method of fabricating sample lamella for TEM analysis as claimed in claim 4, wherein the method of forming the holder on the covering layer comprises using an adhesive.

6. The method of fabricating sample lamella for TEM analysis as claimed in claim 5, wherein the adhesive comprises epoxy.

7. The method of fabricating sample lamella for TEM analysis as claimed in claim 1, wherein the process of forming the mark comprises using a dual beam FIB or laser.

8. The method of fabricating sample lamella for TEM analysis as claimed in claim 1, wherein the mark comprises a groove.

9. The method of fabricating sample lamella for TEM analysis as claimed in claim 1, wherein the backside polishing process comprises a mechanical polishing process.

10. The method of fabricating sample lamella for TEM analysis as claimed in claim 1, wherein the in-situ lift-out step is performed in the dual beam FIB system.

11. The method of fabricating sample lamella for TEM analysis as claimed in claim 10, further comprising a step of forming a protection layer on the bottom surface of the waiting-examination sample before performing the in-situ lift-out step.

12. The method of fabricating sample lamella for TEM analysis as claimed in claim 11, wherein the passivation layer comprises platinum (Pt) or tungsten (W).

13. The method of fabricating sample lamella for TEM analysis as claimed in claim 1, further comprising a step of performing a sample membrane thinning step after performing the in-situ lift-out step.

* * * * *